(12) United States Patent
Sataloff

(10) Patent No.: US 11,406,492 B1
(45) Date of Patent: Aug. 9, 2022

(54) VOCAL FOLD PROSTHESIS AND METHOD FOR REMOVAL OF LARYNGEAL WEB

(71) Applicant: Robert T. Sataloff, Philadelphia, PA (US)

(72) Inventor: Robert T. Sataloff, Philadelphia, PA (US)

( * ) Notice: Subject to any disclaimer, the term of this patent is extended or adjusted under 35 U.S.C. 154(b) by 45 days.

(21) Appl. No.: 17/028,787

(22) Filed: Sep. 22, 2020

(51) Int. Cl.
*A61F 2/20* (2006.01)

(52) U.S. Cl.
CPC ........ *A61F 2/20* (2013.01); *A61F 2220/0075* (2013.01); *A61F 2230/0023* (2013.01)

(58) Field of Classification Search
CPC ............... A61F 2/20; A61F 2220/0075; A61F 2230/0023
USPC ............................................................ 623/9
See application file for complete search history.

(56) References Cited

U.S. PATENT DOCUMENTS

| | | | | |
|---|---|---|---|---|
| 5,531,752 | A * | 7/1996 | Netterville | A61F 2/20 606/99 |
| 6,358,222 | B1 * | 3/2002 | Grundei | A61F 2/203 604/8 |
| 9,675,446 | B2 * | 6/2017 | Jaber | A61F 2/20 |
| 9,700,408 | B1 * | 7/2017 | Sataloff | A61F 2/20 |
| 2008/0188931 | A1 * | 8/2008 | Kwon | A61F 2/20 623/9 |
| 2011/0130834 | A1 * | 6/2011 | Wilson | A61F 2/2412 623/9 |
| 2012/0022389 | A1 * | 1/2012 | Sanders | A61B 17/0401 600/533 |
| 2015/0327993 | A1 * | 11/2015 | Persson | A61F 2/203 623/9 |
| 2017/0135804 | A1 * | 5/2017 | Marten | A61M 16/0465 |
| 2018/0071083 | A1 * | 3/2018 | Fahl | A61F 2/20 |
| 2018/0369527 | A1 * | 12/2018 | Arlinghaus, Jr. | A61M 16/0816 |

* cited by examiner

*Primary Examiner* — Suzette J Gherbi
(74) *Attorney, Agent, or Firm* — Andrew L. Salvatore, Esquire

(57) ABSTRACT

Typically, surgical intervention is required to remedy abnormalities of the vocal cords. However, surgical intervention often causes a laryngeal web, or glottic web, to form which impairs the sound quality of the vocal cords. The prosthesis and methods of the invention effectively eliminate regrowth of a laryngeal web after surgery over all other prior art devices and methodologies. During the operative procedure, the prosthesis may be inserted through a surgically created hole in a laryngeal web allowing a laryngeal bridge to assist in holding the prosthesis in position. Following surgery, after the vocal cords heal, the prosthesis may then be removed, and the laryngeal bridge also removed. In the case of an anterior procedure, the prosthesis produces a sharp anterior commissure without any glottic web. The prosthesis and method greatly reduce the recurrence of a laryngeal web.

17 Claims, 12 Drawing Sheets

VOCAL FOLD PROSTHESIS AND METHOD FOR REMOVAL OF LARYNGEAL WEB

BACKGROUND OF THE INVENTION

Field of Invention

The invention relates to a prosthesis inserted into the anterior or posterior area of the vocal folds to prevent the formation of a laryngeal web after a surgical procedure. A laryngeal web, or glottic web, is a common congenital malformation of the larynx which may range from a thin, translucent diaphragm to a thicker, more fibrotic obstruction spread between the vocal folds near the anterior commissure.

Various conditions give rise to the need for surgical intervention in the larynx. For instance, in the case of recurrent respiratory papillomatosis (RRP), a condition caused by the human papilloma virus (HPV), papillomas, wart-like growths, may grow on the surface of the tissue around the vocal folds. The papillomas most commonly grow in the larynx. These papillomas are typically benign, but tend to recur even after removal of the growths. Papillomas may also form after any surgical procedure, intubation, radiation, or a traumatic event.

Vocal folds have a tendency to develop fibrosis and granulation tissue after surgical intervention. This reparative process often results in the formation of a laryngeal web between vocal folds which impairs vocal quality and causes various symptoms including dysphonia (impairment of voice quality), hoarseness, stridor (noisy breathing), and airway obstruction. The laryngeal web, then, is typically treated by removing the laryngeal web through incision and placement of a stent or keel to keep the vocal folds separated as the vocal folds heal. However, any surgical intervention in the area of the vocal folds may lead to regrowth of a laryngeal web, and the stents which have typically been used have failed to prevent reformation of a laryngeal web in a great number of cases.

Description of the Prior Art

Formation of a glottic web between vocal folds has been a persistent and recurrent problem after surgical intervention involving the vocal folds. Various stents have been placed between the vocal folds in order to maintain the structure and assist in recovery following a surgical procedure. For instance, Haslinger described insertion of a silver plate between vocal cords and passing a wire through thyroid cartilage at the anterior commissure. McNaught described a method of slotting a flanged tantalum keel through a midline incision in the lower two-thirds of the thyroid cartilage to separate vocal cords for two months. However, such keels interfered with swallowing due to its size and shape. Maran described a modified McNaught keel which also incorporated silicone rubber. However, Maran reported that speech was not fully normal after two years although scar tissue had not recurred.

Other larger stents have been used in cases where a laryngeal web has been removed entirely. For instance, Hardingham described a large silastic keel, in the shape of a block, secured between the vocal cords at the anterior commissure. Such a stent has been used after complete removal of a laryngeal web, but is not designed to be utilized within a divided web or stenosis using the abnormal scar tissue to position the web. Larger stents also preclude the patient from speaking until after the stent is removed. Further, these types stents require external fixation with sutures outside the neck and require complete, rather than partial, resection of the stenosis with staged completion. Many of the existing stents and keels require a tracheotomy and require placement through a neck incision rather than endoscopic placement.

Antibiotic mitomycin-C (MMC) has been used to treat patients after surgical removal of a laryngeal web to prevent regrowth, but this treatment also has been shown to affect the vibratory patterns of the vocal folds.

Anterior glottic webs are always a challenge for laryngologists. In order to address the problem of recurrent anterior blunting, a prosthesis has been designed by Dr. Sataloff which provides excellent results over the prior art. In the case of an anterior procedure, following surgery involving insertion of the prosthesis, the vocal cords maintained a sharp anterior commissure and the glottic web did not reform. Further, due to the small size of the prosthesis, a patient's breathing and speech patterns are not diminished while the prosthesis is in place, and voice quality is greatly improved as a result of the surgical procedure using the prosthesis.

SUMMARY OF THE INVENTION

Vocal cords or vocal folds are located within the human larynx and form the sounds of speech and other tones through vibrations as air passes between the vocal cords. However, various diseases may affect the vocal cords and prevent proper functioning. One such condition is recurrent respiratory papillomatosis (RRP) in which papillomas, wart-like growths, may grow on the surface of the tissue around the vocal folds.

Typically, surgical intervention is required to remedy abnormalities of the vocal cords. However, surgical intervention often causes a laryngeal web, or glottic web, to form which impairs the sound quality of the vocal cords. In normal vocal cords, the anterior commissure forms a sharp point of contact. However, when a laryngeal web forms, the sharp point of the anterior commissure is destroyed, and abnormal tissue forms between the vocal cords partially obstructing the flow of air between the vocal cords. A laryngeal web may also form posteriorly within the vocal cords causing similar symptoms.

The prosthesis of the invention greatly reduces regrowth of a laryngeal web after surgery over all other prior art devices and methodologies. The prosthesis of the invention may comprise a corpus and flanges at either end of the corpus. In different embodiments, an anterior vocal fold prosthesis may be used to remove a laryngeal web anteriorly, and similarly, a posterior vocal fold prosthesis may be used to remove a posterior laryngeal web.

During the operative procedure, the prosthesis may be inserted through a surgically created hole in a laryngeal web creating a laryngeal bridge to assist in holding the prosthesis in position. A suture passing may be used to secure the prosthesis to the laryngeal bridge. The prosthesis of the invention does not block the flow of air through the larynx and allows the recipient to speak and breath while the prosthesis is in place.

Following surgery, after the vocal cords heal, the prosthesis may then be removed and the laryngeal bridge excised resulting in complete removal of the laryngeal web. In the case of an anterior procedure, the laryngeal bridge is removed resulting in the existence of a sharp anterior commissure without any glottic web. This procedure greatly reduces the recurrence of a laryngeal web.

Both the anterior and the posterior prostheses should be of sufficient strength such that they will not fall apart when a needle is inserted. Additionally, the prostheses may also include a suture already in place such that the surgeon does not need to thread prosthesis prior to or during the operative procedure.

DETAILED DESCRIPTION OF THE INVENTION

Vocal cords or vocal folds are located within the human larynx and form the sounds of speech and other tones through vibrations as air passes between the vocal cords. Maintaining healthy vocal cords is important for effective communication, singing, and other sounds of human communication. However, various diseases may affect the vocal cords and prevent proper functioning. One such condition is recurrent respiratory papillomatosis (RRP) in which papillomas, wart-like growths, may grow on the surface of the tissue around the vocal folds.

Typically, surgical intervention is required to remedy abnormalities of the vocal cords. However, surgical intervention often causes other problems which impair the sound quality of the vocal cords including dysphonia (impairment of voice quality), hoarseness, stridor (noisy breathing), and airway obstruction, in particular, the formation of a laryngeal web between the vocal folds. In normal vocal cords, the anterior commissure forms a sharp point of contact. However, when the laryngeal web, or glottic web, forms, the sharp point of the anterior commissure is destroyed, and abnormal tissue forms between the vocal cords partially obstructing the flow of air between the vocal cords. A laryngeal web may also form posteriorly within the vocal cords causing similar symptoms.

Figure 1:
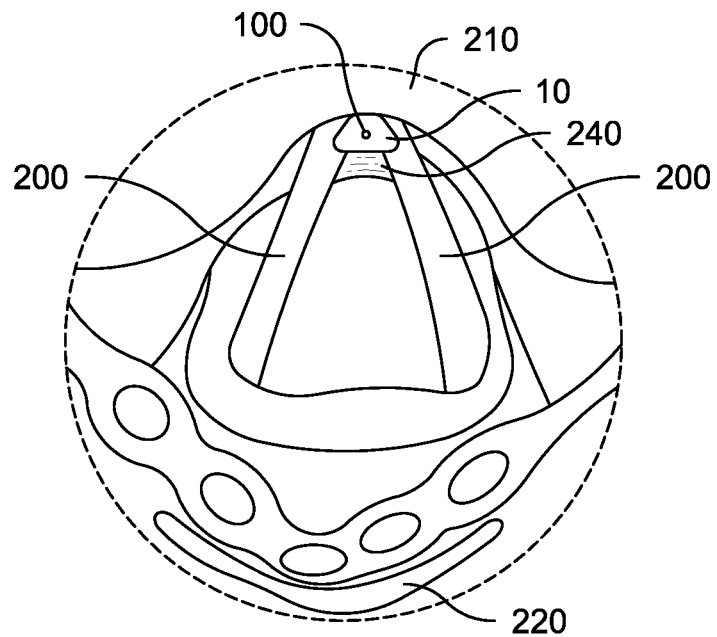
FIG. 1 shows cross sectional view of a human larynx viewed from the top with an anterior vocal fold prosthesis according to the invention.
Figure 2:
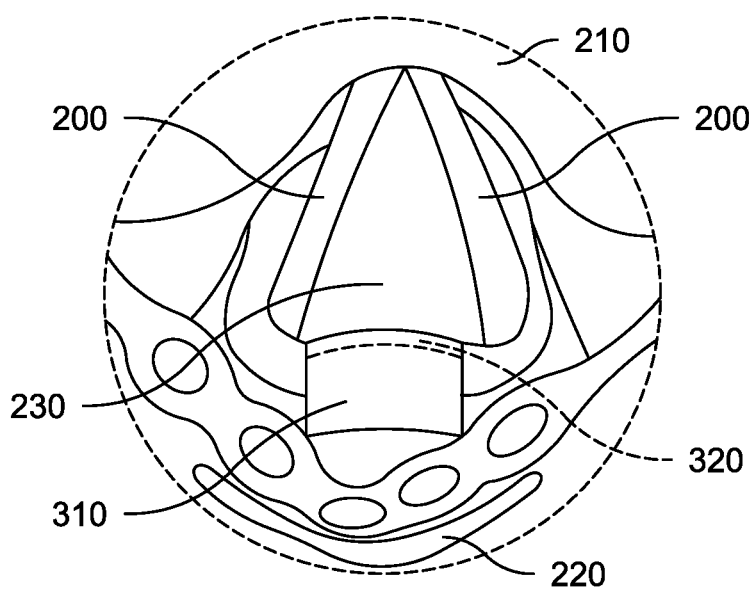
FIG. 2 shows cross sectional view of a human larynx viewed from the top with a posterior vocal fold prosthesis according to the invention.

As shown in FIGS. 1 and 2, vocal cords 200 attach at the epiglottis 210 forming a V shape. Air passes through the larynx 230 and through the vocal cords 200 causing the vocal cords to vibrate and produce sound. The esophagus 220 passes posterior to the vocal cords.

Prior art inventions have focused on removing a laryngeal web in its entirety and inserting a stent between the vocal folds until the vocal cords healed. This procedure often provides less than satisfactory results with the laryngeal web often forming again between the vocal cords. The subject invention provides for an incision through the laryngeal web, leaving a laryngeal bridge, and the prosthesis of the invention inserted into the hole created by the incision. In the case of an anterior procedure, to successfully treat and remove an anterior laryngeal web using the prosthesis of the subject invention, an incision may be made through the laryngeal web at point of the anterior commissure and an anterior vocal fold prosthesis may be placed at the point of incision. The incision may leave a portion of the laryngeal web to form a laryngeal bridge 240. Maintenance of the posterior aspect of the web is important to a successful outcome. Following surgery, the vocal fold prosthesis may stay in place for a clinically effective period of time, usually several weeks, to allow the vocal folds to recover from the surgery. After this time, the prosthesis may be removed, and the laryngeal bridge 240 may be excised from the vocal cords to complete the procedure.

Similarly, in a posterior procedure, an incision may be made through the laryngeal web to form a hole. The incision creates a laryngeal bridge, and the posterior prosthesis may be inserted into the area of the incision. The vocal folds are then permitted to heal with the prosthesis in place. After healing, the prosthesis is removed, and the laryngeal bridge excised. Utilization of this process with the prosthesis of the invention, both anteriorly and posteriorly, has been shown to prevent or greatly reduce the reformation of a laryngeal web.

As shown in FIG. 1, the anterior vocal fold prosthesis may contain a channel 100 through the prosthesis and may be secured using a suture 120 passing through the prosthesis and attached to the residual portion of the laryngeal web, i.e. the laryngeal bridge 240. After the vocal cords heal, the prosthesis may then be removed, and the laryngeal bridge also removed resulting in the existence of a sharp anterior commissure without any glottic web. This procedure and use of the anterior vocal fold prosthesis greatly reduces the recurrence of a laryngeal web, and the vocal folds have been found to maintain a sharp anterior commissure.

Similarly, as shown in FIG. 2, a posterior vocal fold prosthesis may be placed at the posterior portion of the vocal cords in order to remedy and remove a posterior forming laryngeal web. The posterior vocal fold prosthesis may be generally wider than the anterior vocal fold prosthesis and is sized for placement at the posterior side of the vocal cords. The posterior vocal fold prosthesis may be sutured at the posterior side of the larynx 230 and secured to a surgically created laryngeal bridge. In a similar, manner, the posterior vocal fold prosthesis does not block flow of air through the larynx and permits the recipient to function and speak while it is in place. Use of the posterior vocal fold prosthesis also greatly reduces the recurrence of a laryngeal web.

Due to the size and positioning of the anterior vocal fold prosthesis, the recipient is able to speak and breathe while the prosthesis is in place. In a preferred embodiment, the anterior vocal fold prosthesis may range in size from 3 mm to 6 mm in diameter for positioning at the anterior aspect of the vocal folds. In a preferred embodiment, the posterior vocal fold prosthesis may range in width from 10 mm to 15 mm for position at the posterior aspect of the vocal folds. Using either the anterior vocal fold prosthesis or the posterior vocal fold prosthesis, the size of the airway remains unobstructed and the patient is able to maintain his or her pre-operative speech and breathing pattern.

Both the anterior vocal fold prosthesis and the posterior vocal fold prosthesis may be constructed of a flexible yet sturdy material such that they will not break during the operative procedure. Examples of materials which may be used in construction of the prostheses are silicone products such as a silastic silicone elastomer. The prostheses may be fitted with a suture routed through the prostheses such that the prostheses may be easily secured to surrounding structures, in a preferred embodiment, the surgically created laryngeal bridge, internally during the operative procedure.

FIGS. 3-10 show an anterior vocal fold prosthesis. The anterior vocal fold prosthesis may be sized to be placed between vocal folds which form a V shape at the anterior side of the larynx. The anterior vocal fold prosthesis may comprise a top flange 10, a corpus 20, and a bottom flange 30. Generally, the top flange and bottom flange rest above and below the vocal cords, respectively, and assist to hold the prosthesis in position. The top and bottom flanges may also be larger than the overall width of the corpus so as to assist in securing the prosthesis around the vocal folds. The corpus may extend longitudinally and have a first and second end, and top and bottom flanges may be positioned at the ends of the corpus. The corpus may sit generally between the vocal cords to assist in preventing the reformation of a laryngeal web.

Figure 3:
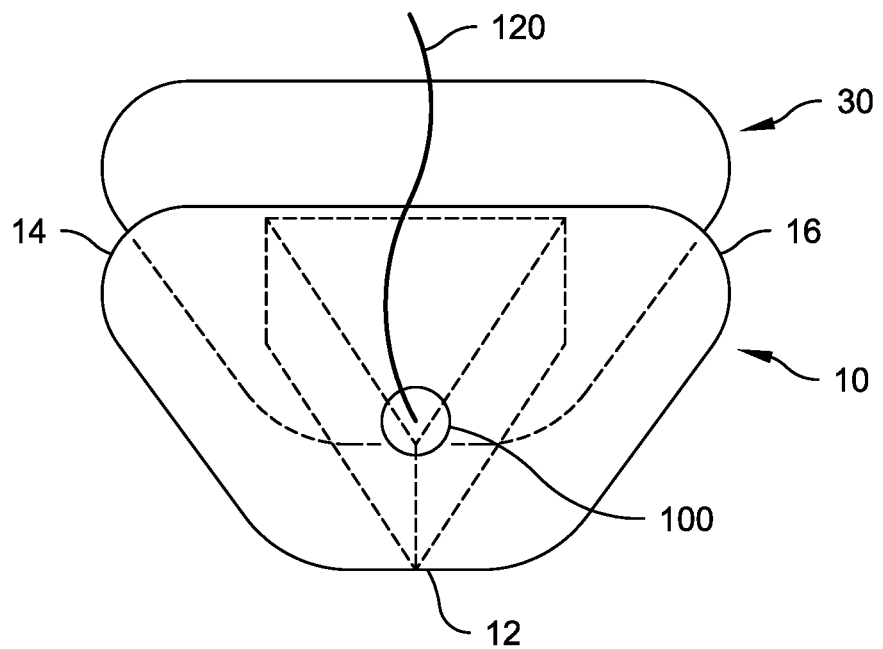
FIG. 3 shows a top plan view of an anterior vocal fold prosthesis according to the invention.
Figure 4:
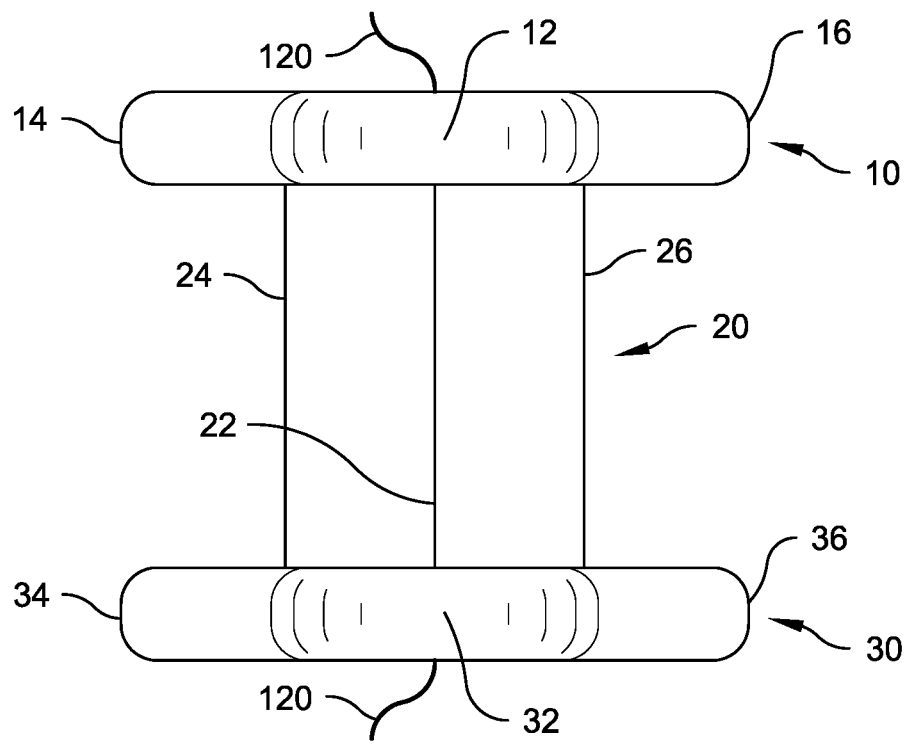
FIG. 4 shows a front elevational view of an anterior vocal fold prosthesis according to the invention.
Figure 5:
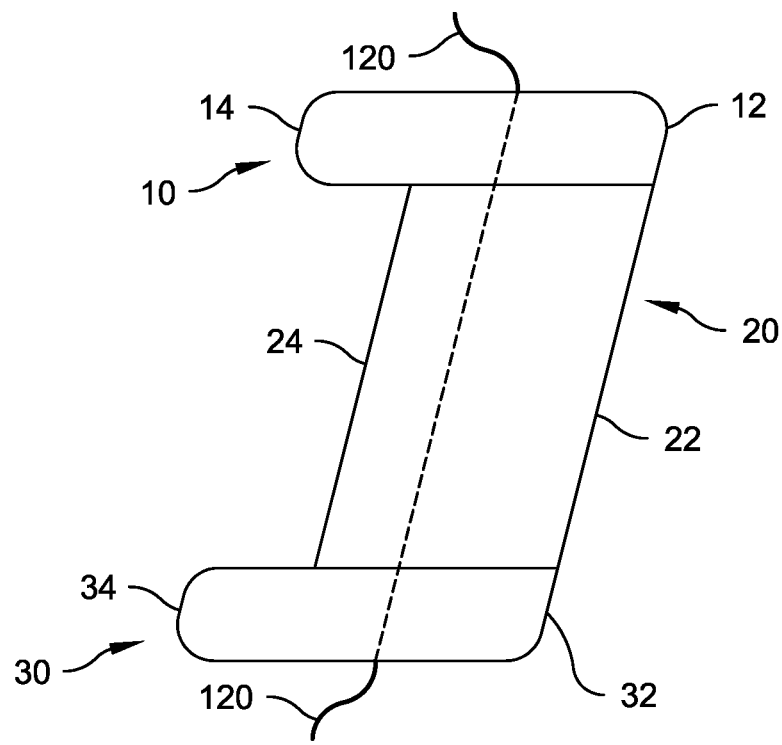
FIG. 5 shows a right side elevational view of an anterior vocal fold prosthesis according to the invention.
Figure 6:
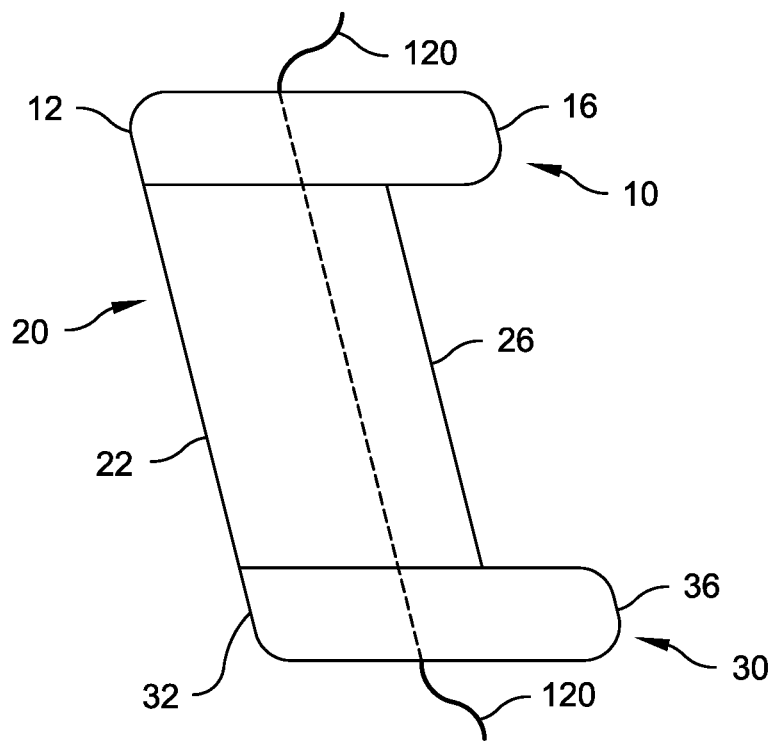
FIG. 6 shows a left side elevational view of an anterior vocal fold prosthesis according to the invention.
Figure 7:
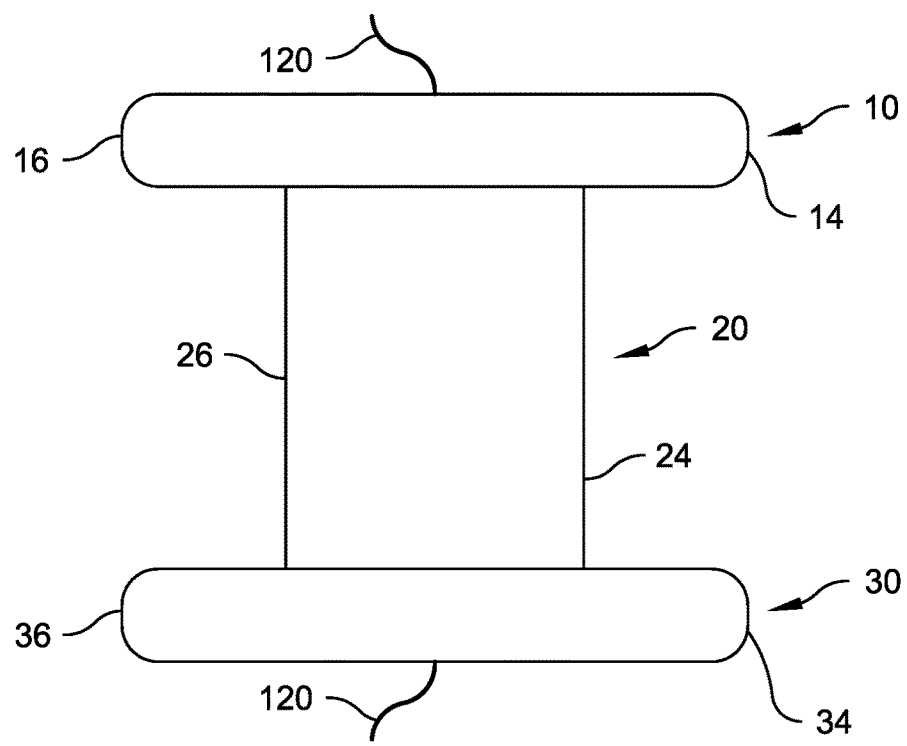
FIG. 7 shows a rear elevational view of an anterior vocal fold prosthesis according to the invention.

FIG. 3 shows a top plan view of an embodiment of the anterior vocal fold prosthesis. The top flange 10 may maintain a generally triangular shape and have top and bottom planar surfaces. The front side of top flange 12 may be placed near the point of the anterior commissure and the right rear corner 14 and left rear corner 16 are located more posteriorly. The flange may contain a channel 100 such that a suture 120 may pass through the top flange 10, through the corpus 20, and the bottom flange 30.

FIGS. 4-7 show front, rear and side views of the anterior vocal fold prosthesis. In a preferred embodiment, the front edge of the corpus 22 maintains a sharp line or point so as to assist in the growth and maintenance of a sharp anterior commissure during the time that the prosthesis is in place. Right rear corner 24 and left rear corner 26 of the corpus are positioned opposite the front edge 22 more posteriorly.

Figure 8:
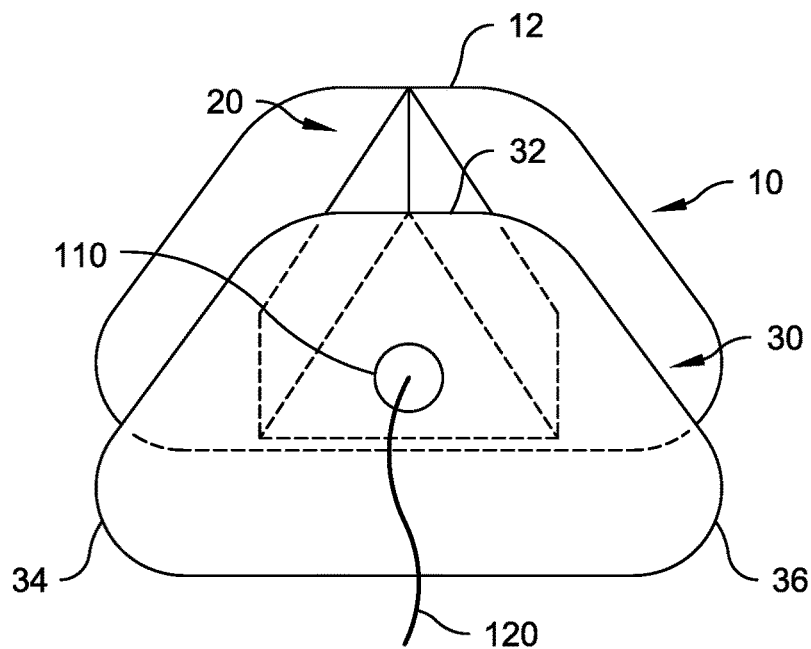
FIG. 8 shows a bottom plan view of an anterior vocal fold prosthesis according to the invention.

FIG. 8 shows a bottom plan view of an embodiment of the anterior vocal fold prosthesis. The bottom flange 30 also may maintain a generally triangular shape and have top and bottom planar surfaces. The front side of bottom flange 32 may be placed near the point of the anterior commissure and the right rear corner 34 and left rear corner 36 are located more posteriorly. The flange may contain a channel 110 such that a suture 120 may pass through the bottom flange 30, through the corpus 20, and the top flange 10.

Figure 9:
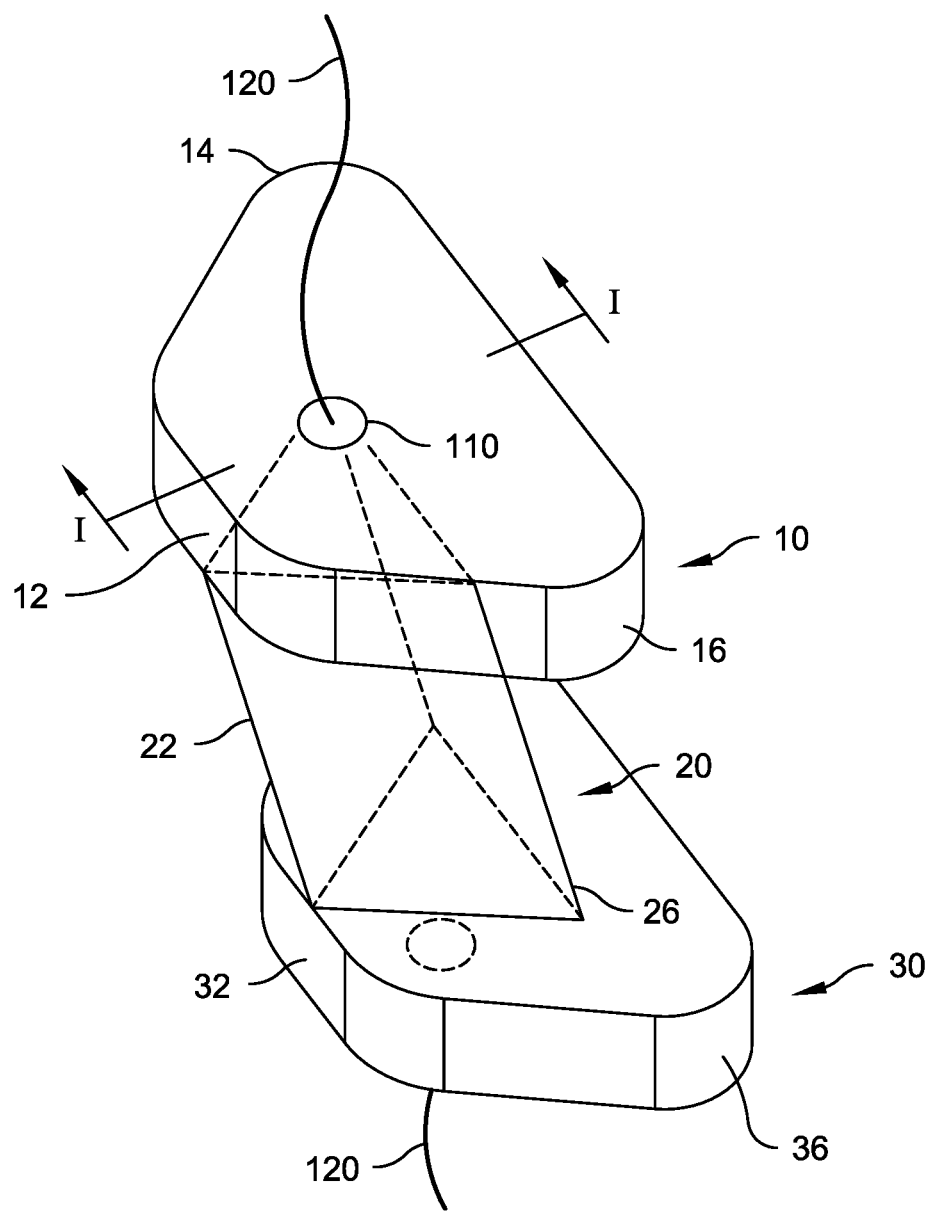
FIG. 9 shows a perspective view of an anterior vocal fold prosthesis according to the invention.
Figure 10:
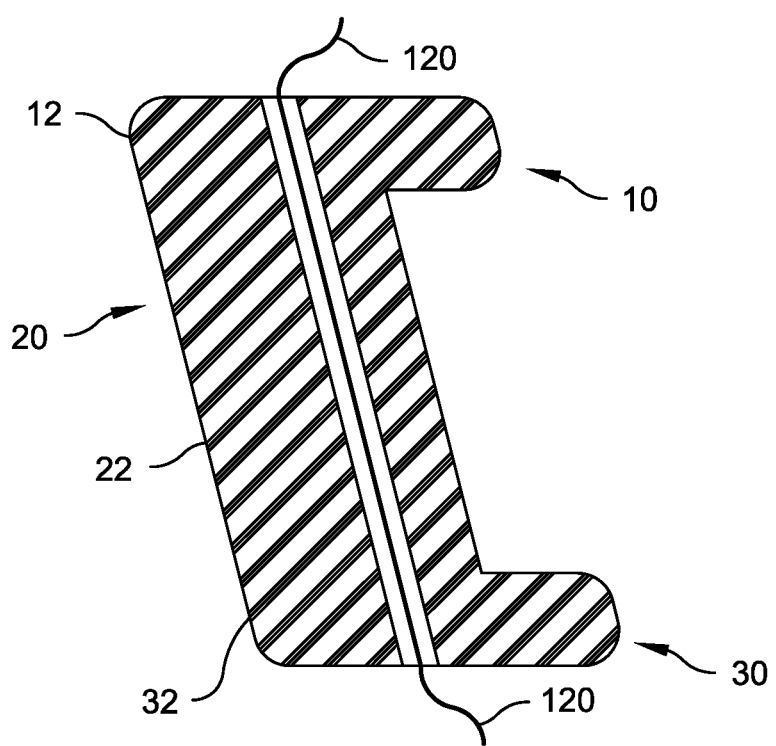
FIG. 10 shows a cross sectional view of an anterior vocal fold prosthesis taken at line I in FIG. 9 according to the invention.

FIG. 9 shows a perspective view of an anterior vocal fold prosthesis, and FIG. 10 shows a cross section view an anterior vocal fold prosthesis taken at line I as indicated in FIG. 9. FIG. 10 demonstrates channel 105 which may pass through the length of the corpus 20 extending also through top 10 and bottom 30 flanges. The channel 105 enables a suture 120 to be placed through the prosthesis which may be used to secure the prosthesis to surrounding tissues internally during the surgical procedure.

Figure 11:
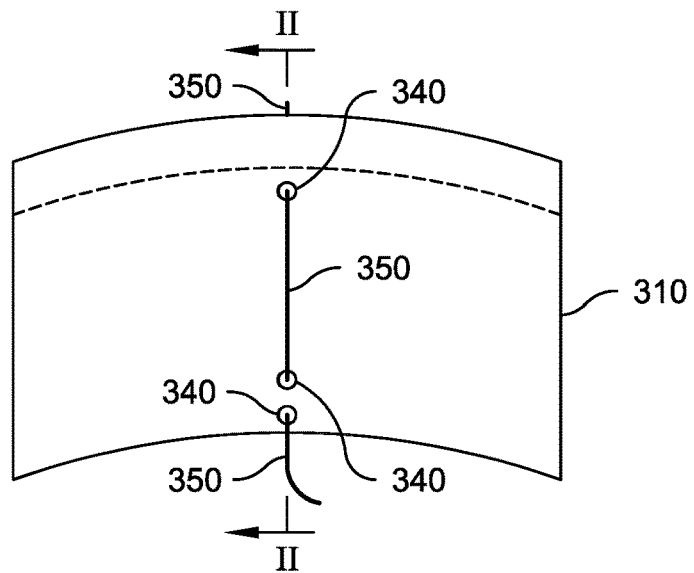
FIG. 11 shows a top plan view of a posterior vocal fold prosthesis according to the invention.
Figure 12:
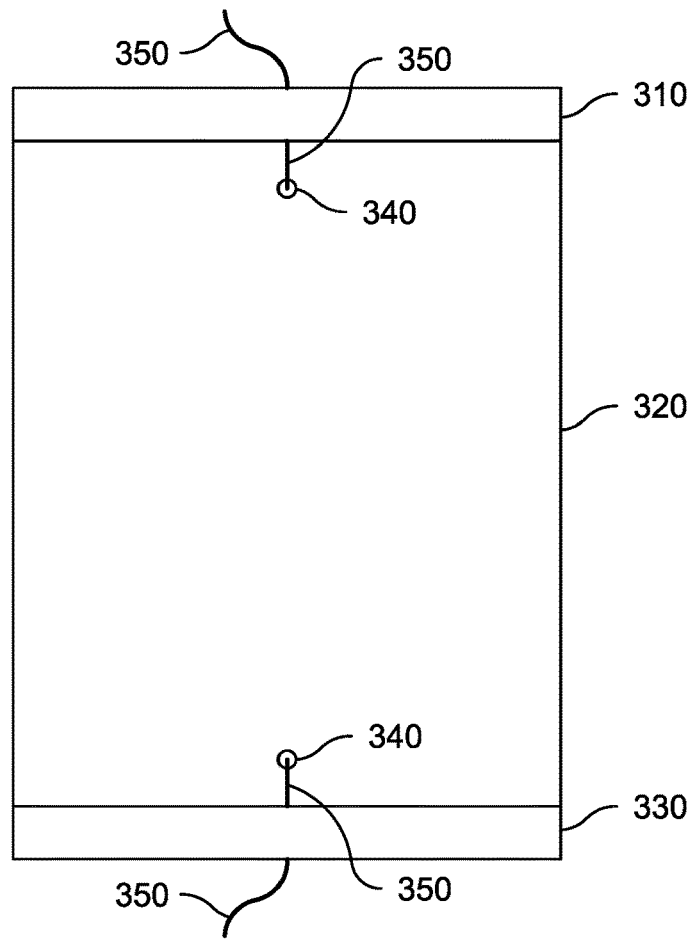
FIG. 12 shows a front elevational view of a posterior vocal fold prosthesis according to the invention.
Figure 13:
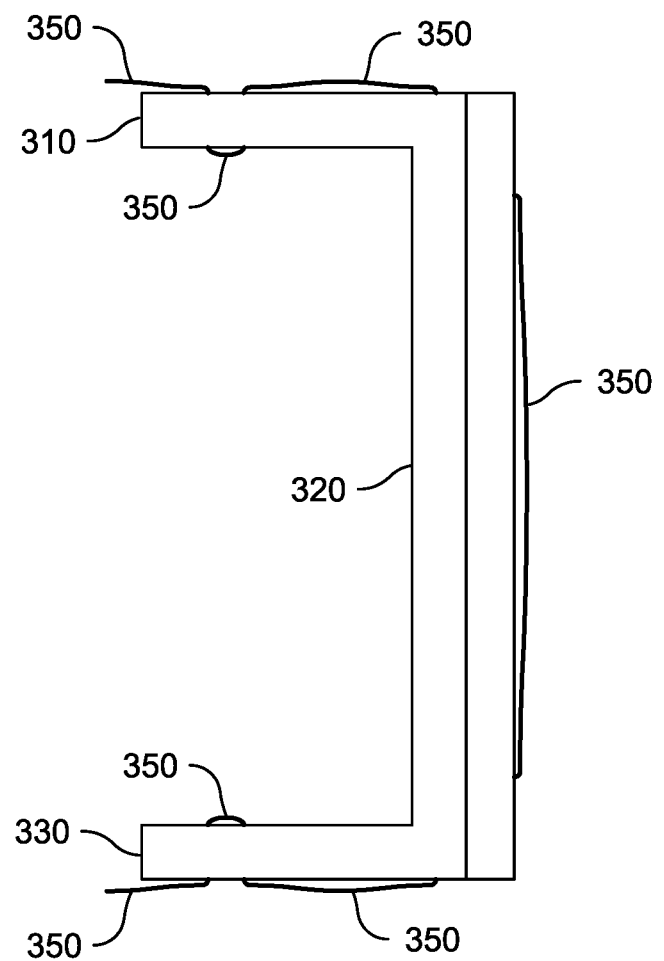
FIG. 13 shows a left side elevational view of a posterior vocal fold prosthesis according to the invention.
Figure 14:
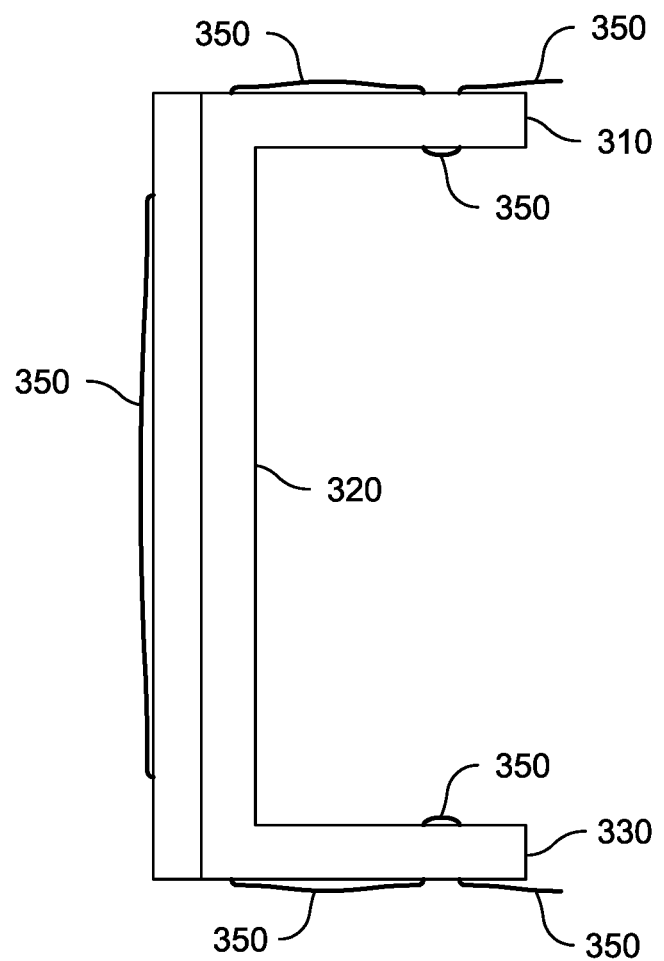
FIG. 14 shows a right side elevational view of a posterior vocal fold prosthesis according to the invention.
Figure 15:
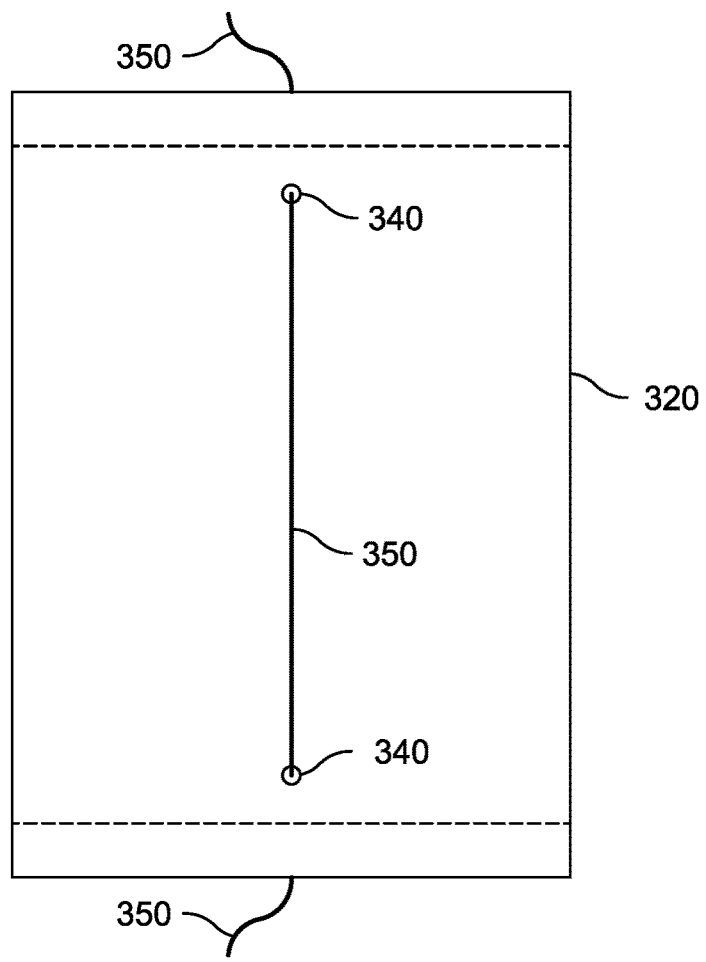
FIG. 15 shows a rear elevational view of a posterior vocal fold prosthesis according to the invention.

FIGS. 11-18 show a posterior vocal fold prosthesis. As shown in FIG. 11, a top flange 310 of the posterior vocal fold prosthesis may be sized for placement between vocal cords at the posterior end and may be slightly curved to comply with the anatomy of the larynx in that region. FIGS. 12-15 show front, side and rear elevational views of the posterior vocal fold prosthesis. Corpus 320 is placed generally between the vocal cords posteriorly and secured in part by top flange 310 and bottom flange 330 which are positioned above and below the vocal cords, respectively. Top flange 310, bottom flange 330, and corpus 320 may contain holes 340 for a suture 350 to pass through the prosthesis to secure it.

Figure 16:
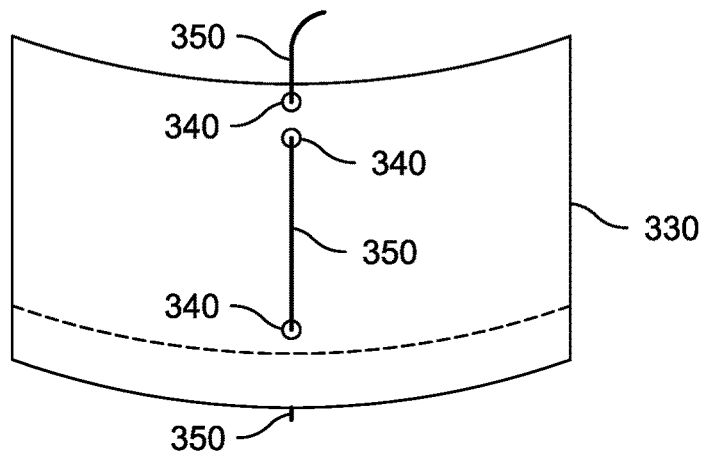
FIG. 16 shows a bottom plan view of a posterior vocal fold prosthesis according to the invention.
Figure 17:
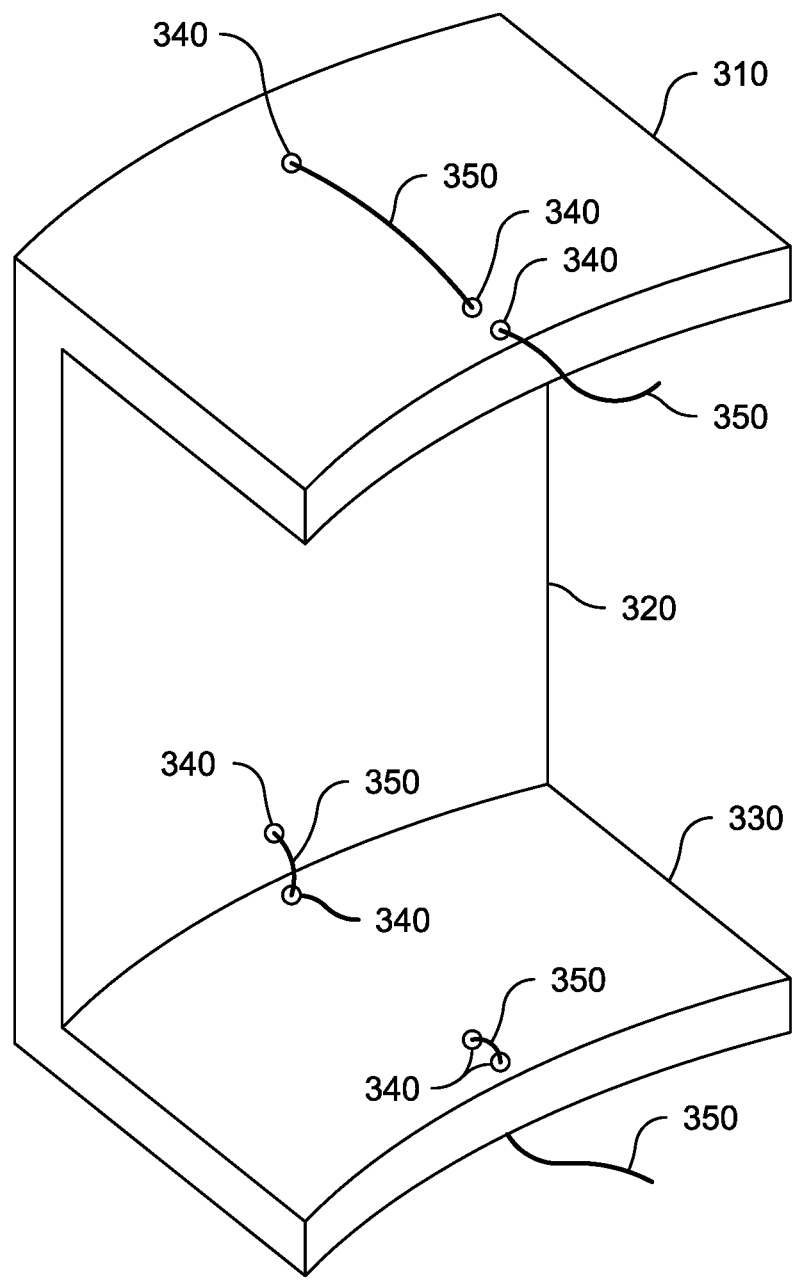
FIG. 17 shows a perspective view of a posterior vocal fold prosthesis according to the invention.

Corpus may maintain a generally rectangular shape, but in a preferred embodiment, may be curved slightly to comply with the anatomy of the larynx in the region. Top and bottom flanges may generally have top and bottom planar surfaces and may have four sides in which two opposite sides may be curved to comply with the anatomy of the larynx in the region. Corpus may have a first end and a second end, and the top flange and bottom flange may be positioned at the first and second end, respectively. FIG. 16 shows the bottom flange 330 which may be sized for placement between vocal cords at the posterior end and may be slightly curved to comply with the anatomy of the larynx in that region. A suture 120 may be threaded through holes 340 of the prosthesis and may be used to secure the prosthesis to surrounding tissues internally during the surgical procedure.

Figure 18:
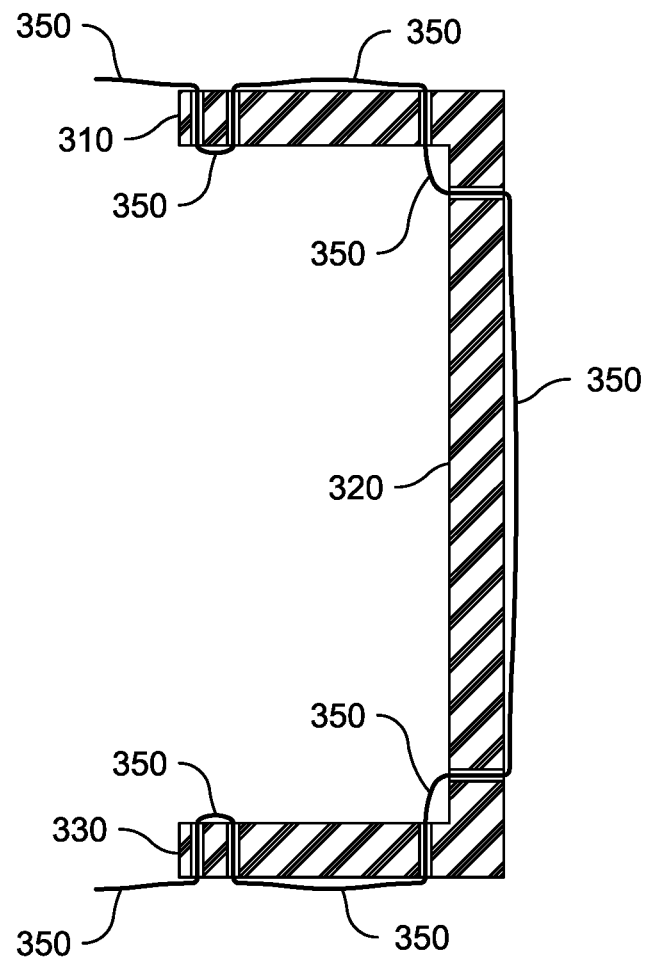
FIG. 18 shows a cross sectional view of a posterior vocal fold prosthesis taken at line II in FIG. 11 according to the invention.

FIG. 18 shows a cross section view a posterior vocal fold prosthesis taken at line II as indicated in FIG. 11. FIG. 18 demonstrates the path of suture 350 as it passes through top flange 310, corpus 320 and bottom flange 330. The positioning of a suture 350 through the prosthesis may be used to secure the prosthesis to surrounding tissues internally during the surgical procedure.

Both the anterior and the posterior prostheses should be of sufficient strength such that they will not fall apart when a needle is inserted. Additionally, the prostheses may also include a suture already in place such that the surgeon does not need to thread prosthesis prior to or during the operative procedure.

Clinical Study

The prosthesis of the invention was utilized in a surgical procedure to prevent recurrence of a laryngeal web in a patient with a history of surgical interventions and resultant growth of laryngeal web. Patient A is a 63 year old teacher with recurrent respiratory papillomatosis (RRP). Prior to treatment with the subject invention, she had over 50 surgeries to correct to her RRP condition. In patients which this condition, glottic webs are common and present several problems, one of which is the surgeon's reluctance to place sutures from the larynx externally because of concerns about creating a trap for spreading of papilloma. Internal stenting has been described in the past, but the prosthesis of the invention improves the outcome of the procedure. In this patient, a thick anterior glottic web was noted after the most recent resection.

Surgery was performed to insert the prosthesis of the invention. Palpation confirmed the presence of lead. An incision was made anteriorly where the anterior commissure should be preserving the posterior portion of the web. A through and through incision was made and a suture was passed through the incision and also through the center of the prosthesis. The prosthesis was tied around the residual web and stabilized.

In three weeks, the prosthesis was removed. At that time, the suture was divided, and the prosthesis was taken out. An anterior commissure had been created and the adjacent areas were mucosalized. Essentially, this created a mucosal bridge in place of a web. Scar tissue was removed the edges made reasonably straight with some scarring. Decadron was injected. Because the anterior portions of the vocal fold were mucosalized, no further stenting was required.

Approximately six months after the surgery, examination confirmed that the vocal folds retained a sharp anterior commissure, and that a glottic web had not formed. Accordingly, the prosthesis resolved the problem of the recurrence of a glottic web.

The invention has been disclosed in terms of preferred embodiments which fulfill all of the objects of the present invention and overcome the limitations of the prior art. It will be understood that each of the elements described above, or two or more together, may also find useful application of other types or methods differing from the types described above. Various changes, modifications, and alterations from the teachings of the present invention may be contemplated by those skilled in the art without departing from the intended spirit and scope thereof. It is intended that the present invention only be limited by the terms of the appended claims.

I claim:

1. An anterior vocal fold prosthesis comprising:
   a corpus extending longitudinally and having a first end and a second end and the corpus having three sides and the corpus having a generally triangular shape,
   a top flange at the first end of the corpus, and
   a bottom flange at the second end of the corpus.

2. An anterior vocal fold prosthesis as in claim 1 wherein the top flange is greater in width that the width of the corpus, and wherein the bottom flange is greater in width than the width of the corpus.

3. An anterior vocal fold prosthesis as in claim 2 wherein the top flange comprises top and bottom planar surfaces, each of the planar surfaces having a generally triangular shape, and the bottom flange comprises top and bottom planar surfaces, each of the planar surfaces having a generally triangular shape.

4. An anterior vocal fold prosthesis as in claim 1 further comprising a channel passing longitudinally through the top flange, the bottom flange, and the corpus.

5. An anterior vocal fold prosthesis as in claim 4 further comprising a suture wherein the suture passes through the channel.

6. An anterior vocal fold prosthesis as in claim 1 wherein an edge formed by two of the sides maintains a sharp line or point.

7. An anterior vocal fold prosthesis as in claim 1 wherein the prosthesis has a diameter in a range from 3 mm to 6 mm.

8. An anterior vocal fold prosthesis as in claim 1 wherein the prosthesis is constructed from a silicone elastomer.

9. A posterior vocal fold prosthesis comprising:
   a corpus extending longitudinally and having a first end and a second end, the corpus having a generally rectangular shape,
   a top flange at the first end of the corpus, and
   a bottom flange at the second end of the corpus.

10. A posterior vocal fold prosthesis as in claim 9 wherein the corpus is curved.

11. A posterior vocal fold prosthesis as in claim 9 wherein the top flange has top and bottom planar surfaces and the top flange having four sides wherein two opposite sides are curved and wherein the bottom flange has top and bottom planar surfaces and the bottom flange having four sides wherein two opposite sides are curved.

12. A posterior vocal fold prosthesis as in claim 9 wherein the corpus, the top flange, and the bottom flange further comprise holes within the corpus, the top flange, and the bottom flange.

13. A posterior vocal fold prosthesis as in claim 12 further comprising a suture wherein the suture passes through the holes.

14. A posterior vocal fold prosthesis as in claim 9 wherein the prosthesis has a width in a range from 10 mm to 15 mm.

15. A posterior vocal fold prosthesis as in claim 9 wherein the prosthesis is constructed from a silicone elastomer.

16. A method for removal of an anterior laryngeal web and preventing regrowth of the laryngeal web comprising:
   creating an incision within a laryngeal web between vocal folds to form a hole bounded by the vocal folds and a surgically created laryngeal bridge,
   inserting an anterior vocal fold prosthesis as in claim 1 into the hole,
   securing the anterior vocal fold prosthesis to the laryngeal bridge with a suture and then allowing the vocal folds to heal for a clinically effective period of time,
   removing the anterior vocal fold prosthesis after the clinically effective period of time, and
   removing the laryngeal bridge.

17. A method for removal of a posterior laryngeal web and preventing regrowth of the laryngeal web comprising:
   creating an incision within a laryngeal web between vocal folds to form a hole bounded by the vocal folds and a surgically created laryngeal bridge,
   inserting a posterior vocal fold prosthesis as in claim 9 into the hole,
   securing the posterior vocal fold prosthesis to the laryngeal bridge with a suture and then allowing the vocal folds to heal for a clinically effective period of time,
   removing the posterior vocal fold prosthesis after the clinically effective period of time, and
   removing the laryngeal bridge.

* * * * *